United States Patent
Cekic et al.

(10) Patent No.: US 6,717,161 B1
(45) Date of Patent: Apr. 6, 2004

(54) APPARATUS AND METHOD PROVIDING SUBSTANTIALLY UNIFORM IRRADIATION OF SURFACES OF ELONGATED OBJECTS WITH A HIGH LEVEL OF IRRADIANCE

(75) Inventors: Miodrag Cekic, Bethesda, MD (US); Boris Geller, Germantown, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 0 days.

(21) Appl. No.: 10/425,835

(22) Filed: Apr. 30, 2003

(51) Int. Cl.[7] .................... H05B 31/04; H01J 37/20
(52) U.S. Cl. ............... 250/504 R; 250/503.1; 250/493.1; 250/365; 362/296
(58) Field of Search ............ 250/504 R, 503.1, 250/493.1, 365; 362/296

(56) References Cited

U.S. PATENT DOCUMENTS

| | | | |
|---|---|---|---|
| 4,010,374 A | 3/1977 | Ramler | |
| 4,048,490 A | 9/1977 | Troue | |
| 4,208,587 A | * 6/1980 | Eastlund et al. | 250/492.1 |
| 4,276,479 A | 6/1981 | Mibu et al. | |
| 4,297,583 A | 10/1981 | Nerod | |
| 4,348,105 A | 9/1982 | Caprari | |
| 4,503,086 A | 3/1985 | Schultz | |
| 4,726,949 A | 2/1988 | Miripol et al. | |
| 4,812,957 A | 3/1989 | Hill | |
| 5,130,553 A | 7/1992 | Amoh | |
| 5,176,782 A | 1/1993 | Ishibashi et al. | |
| 5,211,467 A | 5/1993 | Seder | |
| 5,269,867 A | 12/1993 | Arai | |
| 5,440,137 A | * 8/1995 | Sowers | 250/504 R |
| 5,494,576 A | 2/1996 | Hoppe et al. | |
| 5,635,133 A | 6/1997 | Glazman | |
| 5,699,185 A | 12/1997 | MacDonald et al. | |
| 5,760,408 A | 6/1998 | Kikuchi et al. | |
| 5,817,276 A | 10/1998 | Fencl et al. | |
| 5,839,078 A | 11/1998 | Jennings et al. | |
| 5,898,809 A | 4/1999 | Taboada et al. | |
| 5,922,605 A | 7/1999 | Feurstein et al. | |
| 5,932,886 A | 8/1999 | Arai et al. | |
| 5,973,331 A | 10/1999 | Stevens et al. | |
| 6,124,600 A | 9/2000 | Moroishi et al. | |
| 6,128,030 A | 10/2000 | Kikuchi et al. | |
| 6,190,016 B1 | 2/2001 | Suzuki et al. | |

* cited by examiner

Primary Examiner—Nikita Wells
(74) Attorney, Agent, or Firm—Antonelli, Terry, Stout & Kraus, LLP

(57) ABSTRACT

Apparatus for providing substantially two-dimensionally uniform irradiation of elongated three-dimensional objects while the objects are rotating and moving across the irradiator, with a high level of irradiance and with a substantially constant radiation dose on surfaces of the objects during each phase of the rotation and movement. At least one source of radiation produces radiation to irradiate the surfaces of the objects. Each of the sources of radiation is within a respective elongated elliptical reflecting trough and is spaced from the focal axis of the respective trough. Each trough terminates in an opening defining a rectangular plane substantially perpendicular to the major axis of the ellipse of the respective trough and substantially parallel to the longitudinal axis of the respective radiation source. Reflectors extend from the trough substantially to the path of the objects.

16 Claims, 13 Drawing Sheets

APPARATUS AND METHOD PROVIDING SUBSTANTIALLY UNIFORM IRRADIATION OF SURFACES OF ELONGATED OBJECTS WITH A HIGH LEVEL OF IRRADIANCE

FIELD OF THE INVENTION

The present invention pertains to an apparatus for and a method of uniformly projecting a high level of radiation onto elongated three-dimensional objects so as to uniformly treat the surfaces of the objects. More particularly, the present invention pertains to an apparatus and a method providing substantially two-dimensionally uniform irradiation of elongated three-dimensional objects while the objects are rotating and moving across the irradiator, with a high level of irradiance and with a constant radiation dose on the surfaces of the objects during each phase of the rotation and movement.

BACKGROUND OF INVENTION

Various manufacturing processes include treating an object having an elongated three-dimensional surface, such as a curved surface, by irradiating the surface with, for example, ultraviolet (UV) light or other radiation. The radiation treatment may be related to curing, surface modification, disinfection, advanced oxidation or some other procedure. By way of example, in some printing processes a printed pattern is cured by irradiating the pattern. Obtaining a high quality, uniform product requires irradiating a two-dimensionally uniform high level of radiation over the entire object area of interest. Otherwise irregularities in the finished product may result.

Existing devices often expose the central area of an irradiated surface to more radiation than the edge areas of the surface. The areas of high radiation may receive more than the desired level, possibly causing damage, while the areas of low radiation may be undertreated.

Various techniques have been used in the past to control the uniformity of irradiation of planar target surfaces. By way of example, U.S. Pat. No. 4,010,374 discloses an UV light processor including a primary light source which exposes a target surface on a work piece to UV light, with the UV flux incident per unit area of the target surface greater in the central region of the surface than at edges of the surface, and a secondary light source, which is located in a different plane than the primary light source and which exposes the target surface to UV light, with the UV flux incident per unit area of the surface greater at the edge areas of the target surface than at the central region. Not only is such an UV light processor complex and expensive to manufacture and to operate, but also it is difficult to control in a manner that maintains the UV radiation received at the edge areas of the target surface from the secondary source at substantially the same level as the UV radiation received at the central area of the target surface from the primary source.

U.S. Pat. No. 4,276,479 discloses a tunnel type irradiation chamber through which an object to be treated is conveyed. A plurality of cylindrical UV-lenses are within the tunnel type chamber. Two sets of radiation sources, providing light of two different wavelengths, are within the chamber, providing irradiation in two stages. This apparatus is also complex to control, but yet it may not provide uniform radiation distribution on the object surface.

U.S. Pat. No. 4,348,015 shows a radiation projection system including complex lenses in order to provide uniform irradiance. Numerous other systems have been attempted. These generally are complex and expensive, both to construct and to operate. Even so, they generally have difficulty in achieving uniform irradiance, especially two-dimensionally uniform irradiance of elongated curved objects.

SUMMARY OF INVENTION

The present invention is an apparatus and a method providing substantially two-dimensionally uniform irradiation of elongated three-dimensional objects with a high level of radiation. While the present invention is described hereinbelow with reference to irradiation of curved objects, it is to be understood that it is equally applicable to other three-dimensional objects. In accordance with the present invention at least one source is provided for producing radiation to irradiate an elongated curved object surface. Each source may include an elongated discharge bulb. Each radiation source is arranged within a corresponding elongated elliptical reflecting trough, with the radiation source spaced from the focal axis within the trough. Preferably, planar reflectors extend from the troughs to the target surface. Preferably, also, these reflectors are pivotally attached to the troughs so as to accommodate various sizes of target surfaces and to aid in optimization of the uniformity of the radiation distribution. Additionally, preferably each radiation source is on the major axis of the ellipse defining its trough and is spaced from the focal axis within the trough. Further, preferably, the position of each reflecting trough is adjustable in the direction of the minor axis of the ellipse defining the trough. Each source of radiation can be a light source, preferably a source of ultraviolet light such as a microwave electrodeless discharge bulb, an arc discharge bulb, or a fluorescent discharge bulb. The objects are moved past the radiation source and are rotated at a linear speed and an angular velocity determined by the desired dose of radiation.

BRIEF DESCRIPTION OF THE DRAWINGS

These and other aspects and advantages of the present invention are more apparent from the following detailed description and claims, particularly when considered in conjunction with the accompanying drawings. In the drawings:

DETAILED DESCRIPTION OF PREFERRED EMBODIMENTS

In the following description of the present invention, reference is made to the accompanying drawings which form a part hereof and in which are shown by way of illustration various embodiments in which the invention may be practiced. It is to be understood that other embodiments may be utilized and that structural and functional modifications may be made without departing the scope of the present invention.

FIGS. 1–9 illustrate a first embodiment of an irradiation apparatus and method in accordance with the present invention. Apparatus 13 includes a radiation source 7, which is depicted as an elongated discharge bulb having a longitudinal axis. By way of example, in this embodiment radiation source 7 might be a six-inch long, 2400-watt ultraviolet lamp. Radiation source 7 is positioned within a trough 1. Trough 1 preferably is substantially one-half of an elliptical cylinder defined by an ellipse having a major axis, the direction of which is shown by arrow 27, although the trough cross section could be less or more than one-half of an ellipse if desired. Trough 1 has a first focal axes 10 within the trough and a second focal axis 11 outside the trough. Focal axes 10 and 11 are parallel to the longitudinal axis of radiation source 7.

Figure 3:
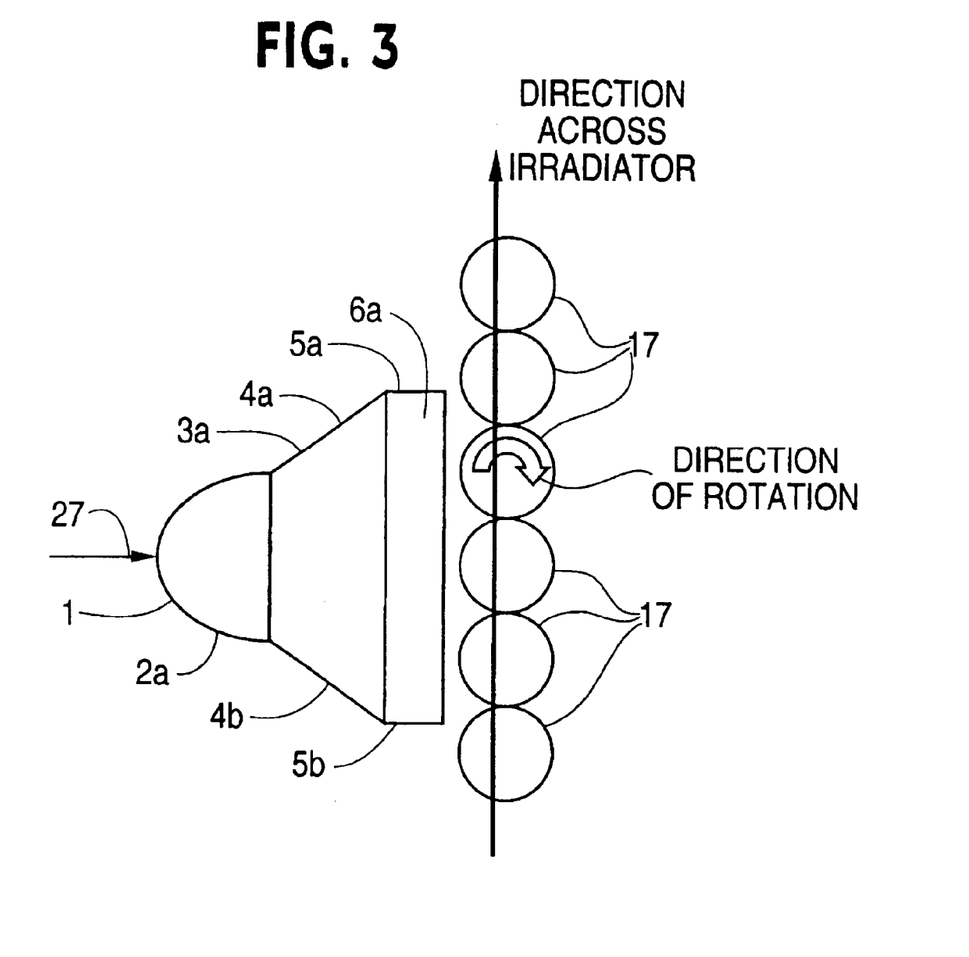
FIG. 3 is a top view of the embodiment of FIG. 1, illustrating relative locations of the apparatus, the direction of the major axis of the ellipse defining the trough, and the irradiated objects, and exemplary directions of linear movement and rotation of the objects.
Figure 4:
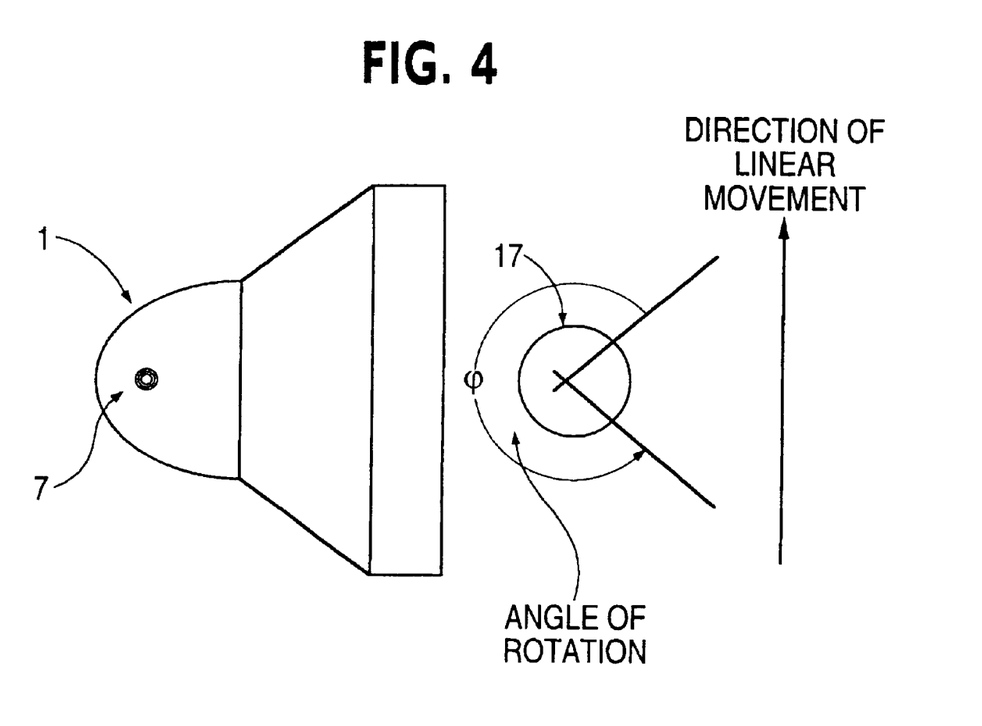
FIG. 4 is a top view of the embodiment of FIG. 1, illustrating the angle of rotation and direction of linear movement of an object undergoing radiation.
Figure 5:
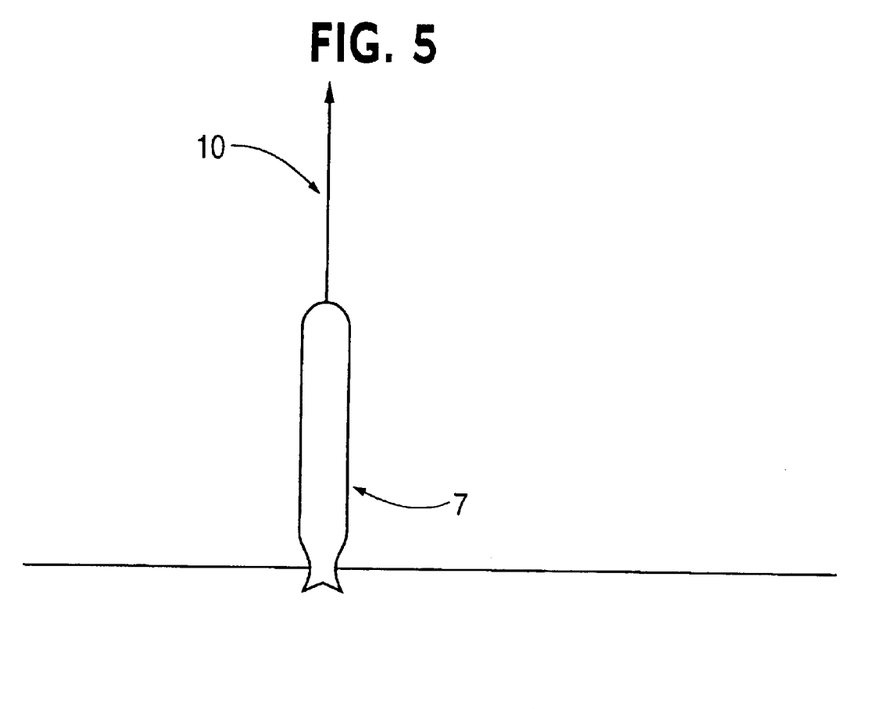
FIG. 5 is a fragmentary view of a bulb suitable for use in an apparatus for providing irradiation of an elongated curved object surface in accordance with the present invention, illustrating relative locations of the bulb and the focal axis of its trough.
Figure 6:
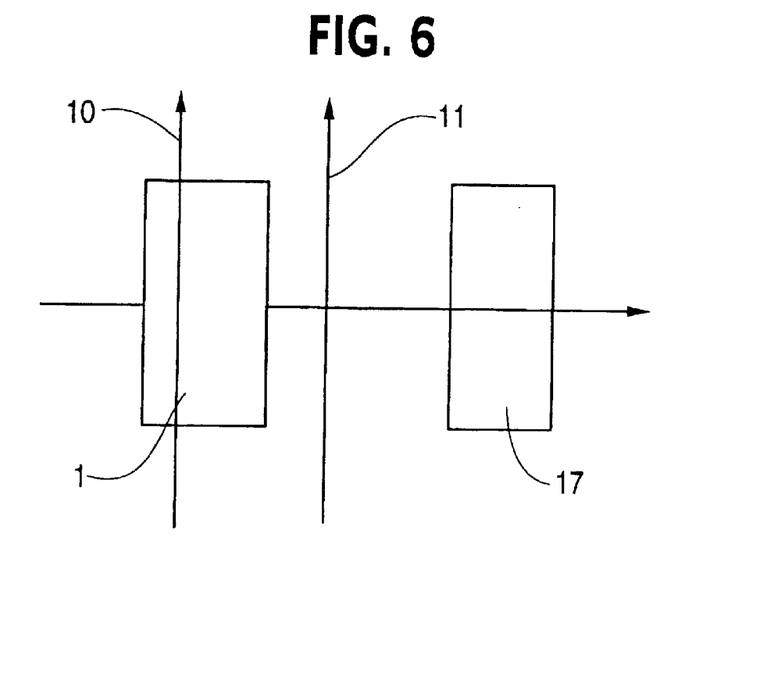
FIG. 6 is a side view of the embodiment of FIG. 1, illustrating relative locations of the trough, the first and second focal axes of the trough, and the object being irradiated.
Figure 7:
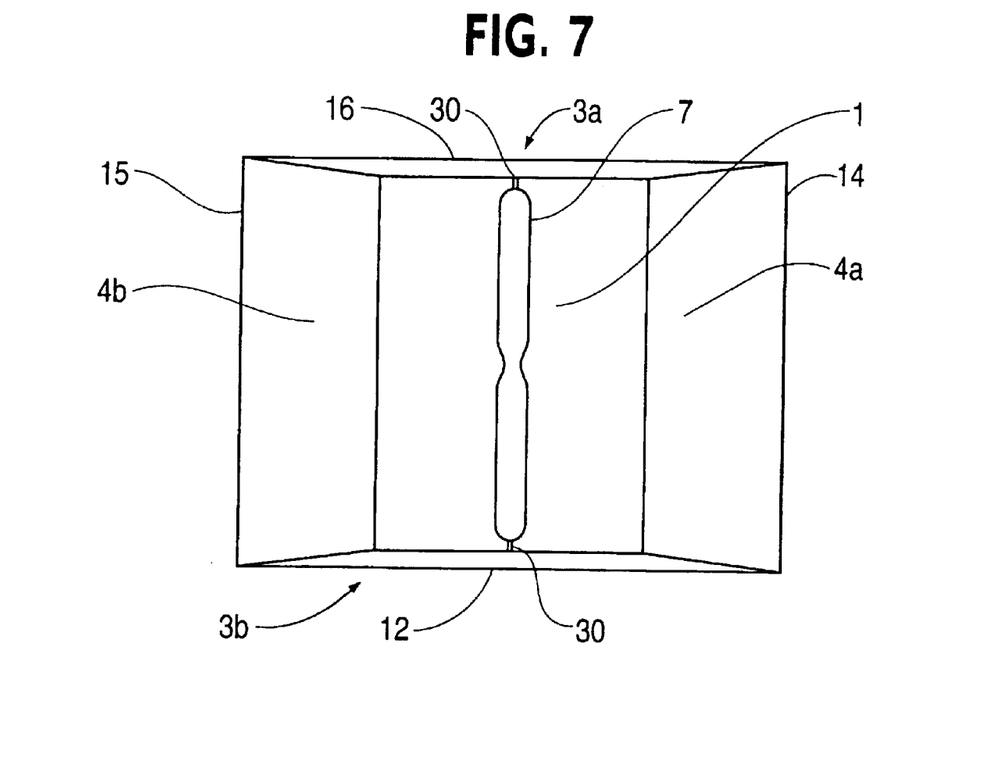
FIG. 7 is a front view of the embodiment of FIG. 1.

Radiation source 7 irradiates one or more elongated curved objects 17 as the objects move in the direction across the irradiator while rotating. In a production process, a plurality of objects 17 might be moved in a line across the irradiator, as depicted in the FIG. 1, or objects may be processed one at a time, with the figures depicting successive positions of the object during its movement. FIGS. 3 and 4 illustrate irradiated objects 17 moving linearly across irradiation apparatus 13 while rotating through an angle φ. In some processes it might be desired to irradiate the entire surface of the object, providing full azimuthal illumination—i.e., φ=2π. In certain processes several rotations of the object might be desired—i.e., φ>2π. In other processes, it may be desired to irradiate only a selected sector of the surface of the object—i.e., φ<2π—as depicted in FIG. 4.

The angular velocity ω of the object 17 as it rotates during movement along the path of travel is determined by the desired dose of radiation and is defined by ω=φV/L, where L is the illuminated length of the path of travel and V is the linear speed of the object 17 through that illuminated length. In a typical process providing full azimuthal illumination (φ=2π) with the illuminated length of the path L=20 cm, the objects might move at a linear speed of from about 1 cm/sec. to about 500 cm/sec., while rotating at a rate of from about 0.05 revolutions per second to about 25 revolutions per second.

The ellipse of trough 1 has a first focal point within the trough and a second focal point outside the trough. The locus of the first focal point along the length of trough 1 defines a first focal axis 10 of the trough, while the locus of the second focal point defines a second focal axis 11. Radiation source 7 is spaced from the first focal axis 10 and object 17 is spaced from the second focal axis 11 at positions on the major axis of the ellipse which defines trough 1 that results in optimum two-dimensional uniformity of the radiation distribution on elongated curved object 17. For source 7 this might be a position toward elongated curved object 17 by, for example, about ten percent of the focal length of the ellipse. For object 17 this might be a position spaced from radiation source 7 by, for example, about 150 percent of the focal length of the ellipse.

Elliptical reflecting trough 1 terminates in a right side edge 9a and a left side edge 9b. Edges 9a and 9b of trough 1 define a plane which is substantially perpendicular to the major axis of the ellipse of trough 1 and substantially parallel to the longitudinal axis of radiation source 7. The upper end of trough 1 is closed by a substantially flat upper elliptical reflector 2a which terminates in an upper forward edge 8a. Similarly, the lower end of trough 1 is closed by a substantially flat lower elliptical reflector 2b which terminates in a lower forward edge 8b.

A substantially flat right side middle reflector 4a extends from right side edge 9a of trough 1 to a substantially flat right side outer reflector 5a. In like manner, a substantially flat left side middle reflector 4b extends from left side edge 9b of trough 1 to a substantially flat left side outer reflector 5b. A substantially flat upper middle reflector 3a extends from upper forward edge 8a of upper elliptical reflector 2a to the inner edge of substantially flat upper outer reflector 6a. In like manner, a substantially flat lower middle reflector 3b extends from lower forward edge 8b of lower elliptical reflector 2b to the inner edge of a substantially flat lower outer reflector (not shown). The right side outer reflector 5a extends from the outer edge 14 of the right side middle reflector 4a toward the objects 17. In like manner, the left side outer reflector 5b extends from the outer edge 15 of the left side middle reflector 4b toward the objects 17. The upper outer reflector 6a extends from the edge 16 of the upper middle reflector 3a toward the objects 17. In like manner, the lower outer reflector extends from the edge 12 of the lower middle reflector 3b toward the objects 17.

Preferably, the several reflectors are mounted by pivotal mounts 28 and telescope so as to accommodate objects 17 of various sizes and to optimize the uniformity of the radiation intensity. Preferably, also, radiation source 7 is mounted on adjustable mounts 30 to permit adjustment of the distance along major axis that source 7 is positioned from first focal axis 10. Likewise, preferably, the position of reflecting trough 1 is adjustable in the direction of the minor axis of the ellipse of the trough. These position adjustments aid in optimization of the two-dimensional uniformity of the radiation.

Although in FIGS. 1–9 and the related description trough 1 and elongated discharge bulb 7 are depicted and described as having their longitudinal axes extending vertically, the axes could extend horizontally or at an angle, if desired.

Figure 1:
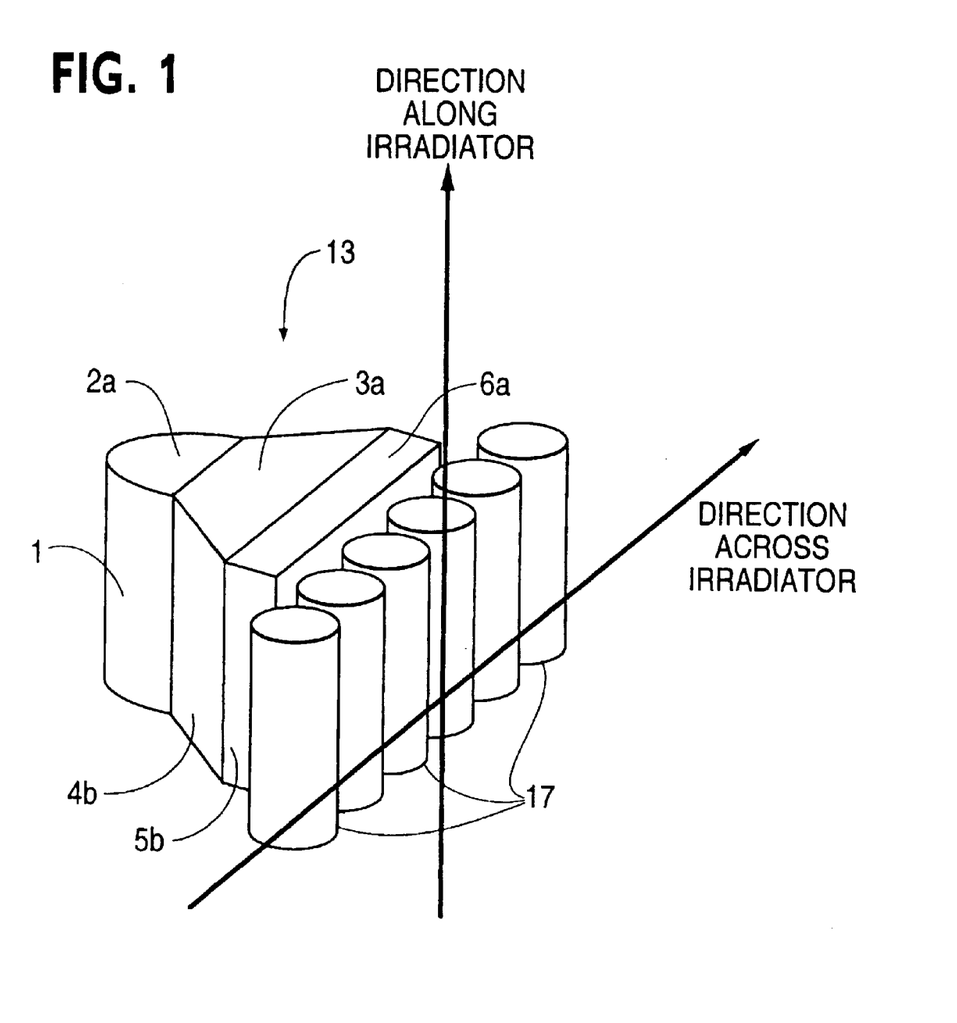
FIG. 1 is an isometric view of a first embodiment of an apparatus providing substantially two-dimensionally uniform irradiation of the surfaces of elongated curved objects in accordance with the present invention.
Figure 2:
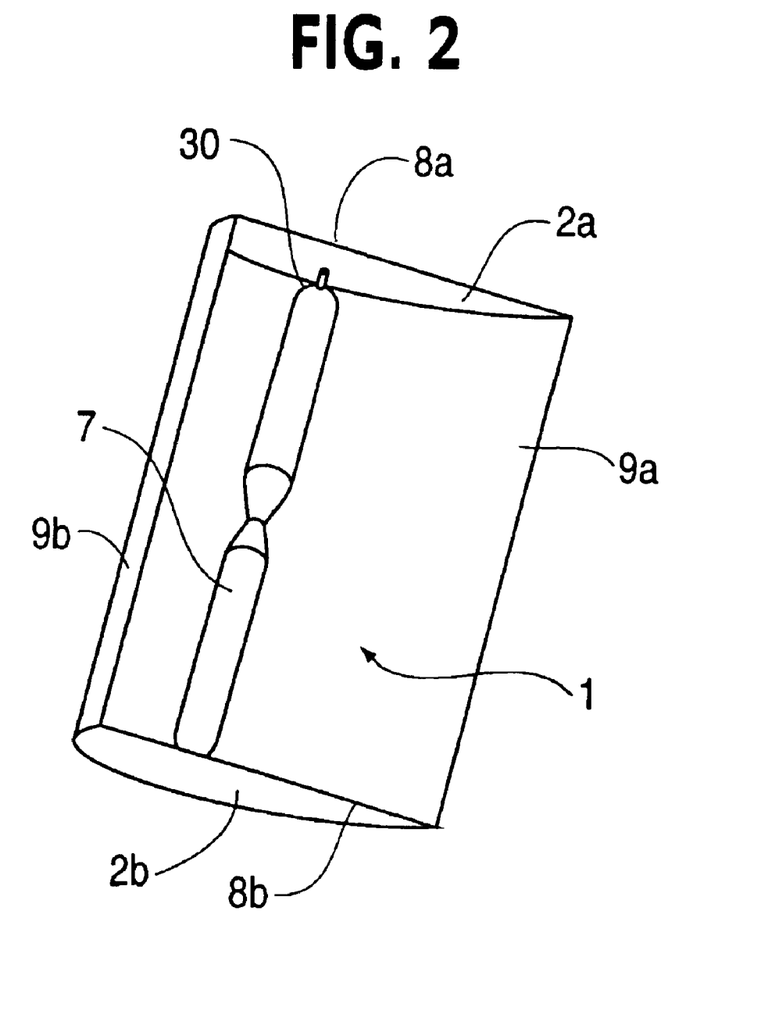
FIG. 2 is an isometric view of an elliptical reflecting trough, with a bulb installed in the trough, suitable for use in an apparatus for providing substantially two-dimensionally uniform irradiation of an elongated curved object surface in accordance with the present invention.
Figure 8:
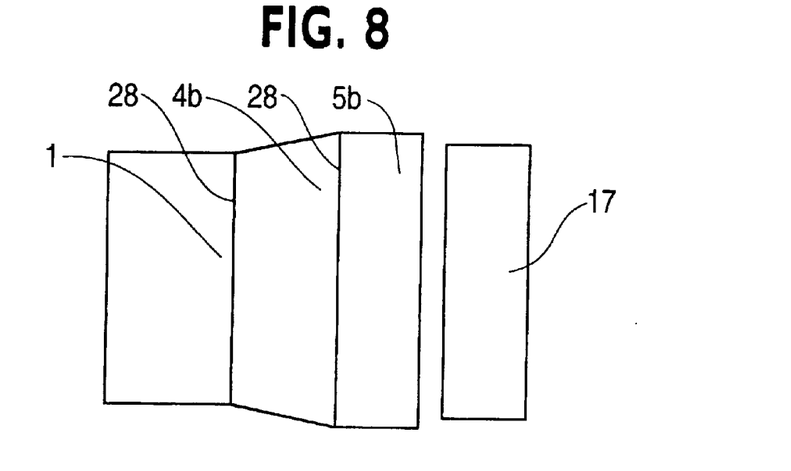
FIG. 8 is a view of the embodiment of FIG. 1 from the left side as seen in FIG. 7.
Figure 9:
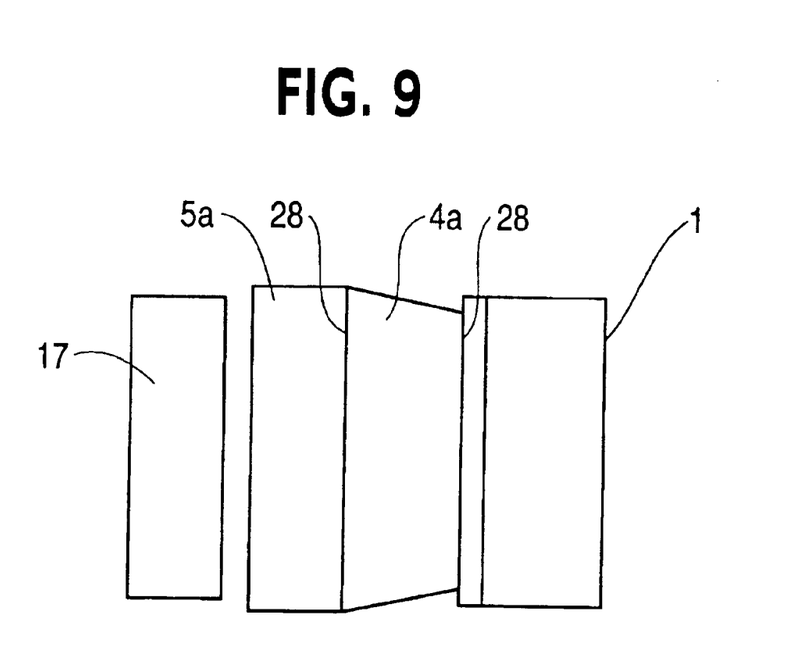
FIG. 9 is a view of the embodiment of FIG. 1 from the right side as seen in FIG. 7.
Figure 10:
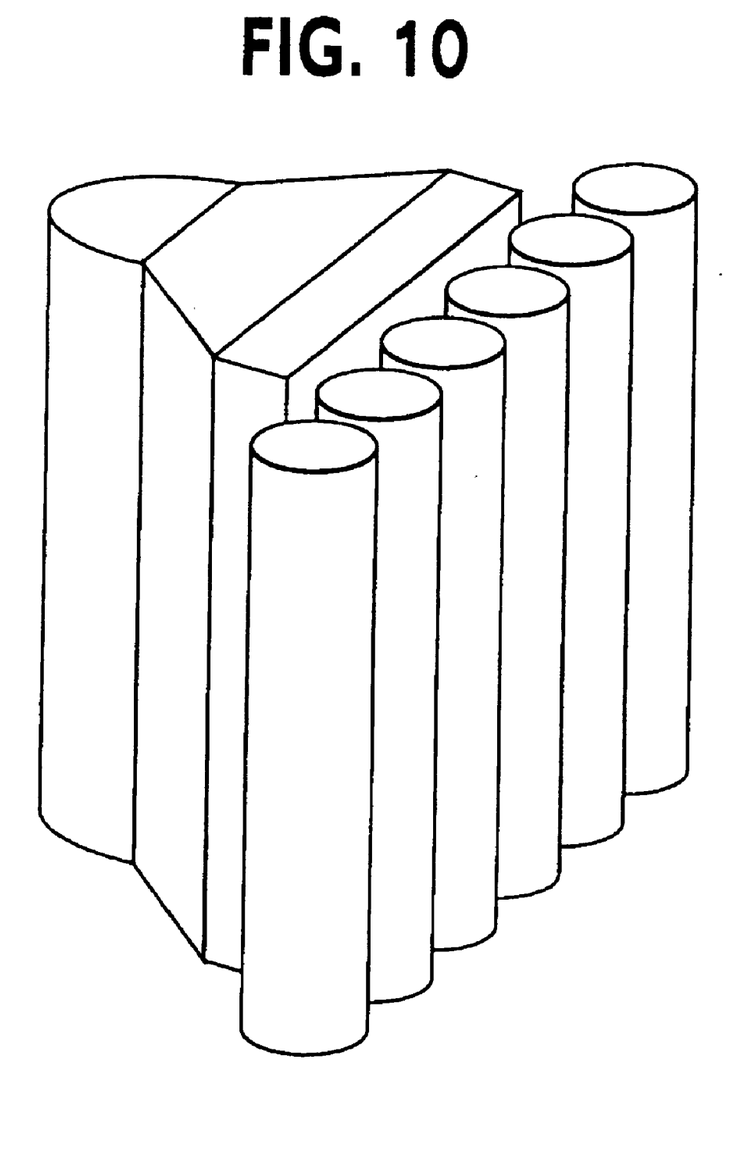
FIG. 10 is an isometric view of a variation of the embodiment of FIG. 1, having increased length of the trough, bulb and flat reflectors for irradiation of longer objects.

FIG. 8 is an isometric view of a variation of the embodiment of FIG. 1, having a longer trough, bulb, and side reflectors for irradiation of longer objects.

Figure 11:
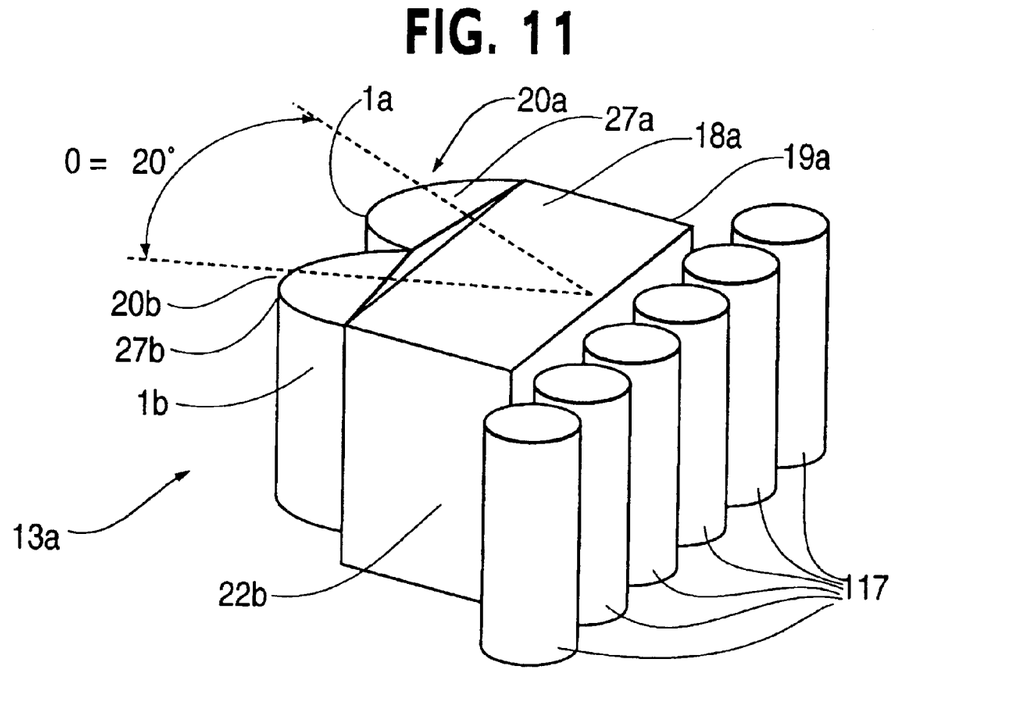
FIG. 11 is an isometric view of a second embodiment of an apparatus for providing substantially two-dimensionally uniform irradiation of an elongated curved object surface in accordance with the present invention.
Figure 12:
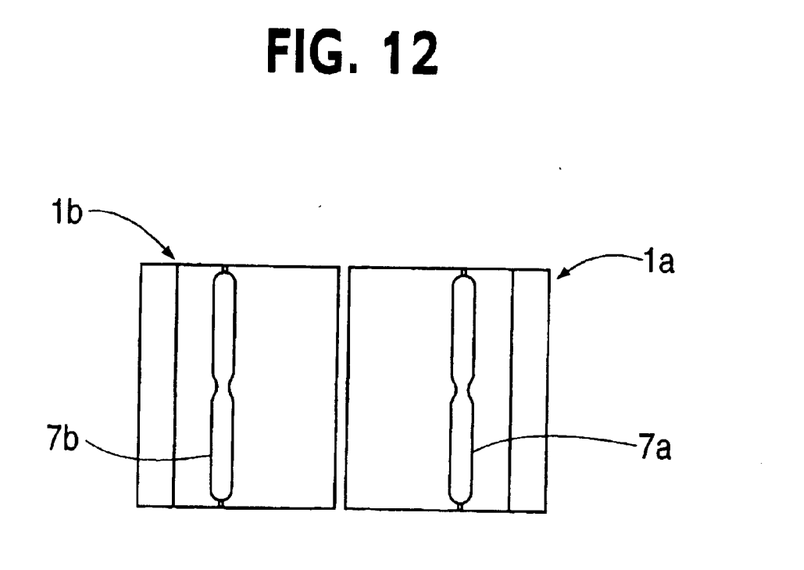
FIG. 12 is a front view of the embodiment of FIG. 11.
Figure 13A:
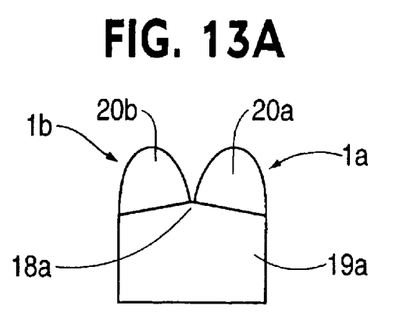
FIGS. 13A and 13B are, respectively, top and bottom views of the embodiment of FIG. 11.
Figure 13B:
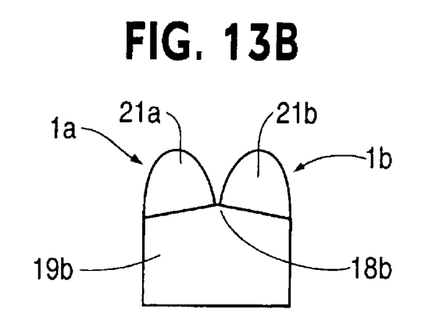
Figure 14A:
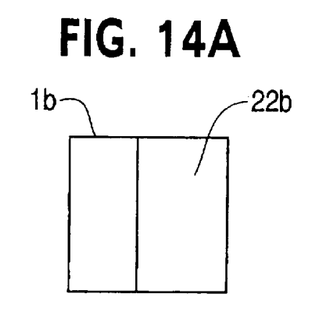
FIGS. 14A and 14B are, respectively, left and right side views of the embodiment of FIG. 11.
Figure 14B:
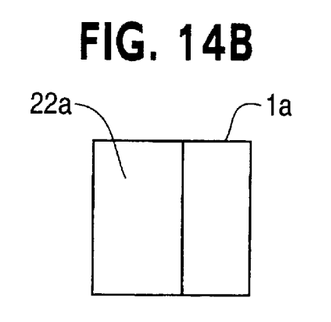

FIGS. 11–14 illustrate a second embodiment of an irradiation apparatus 13a and method in accordance with the present invention. Apparatus 13a includes at least two devices, such as described in the first embodiment, which may have the major axes of the respective ellipses turned slightly so as to intersect at an angle θ for irradiation of shorter objects when a higher level of irradiance is needed. Thus, apparatus 13a includes at least two radiation sources 7a and 7b, each of which is depicted as an elongated discharge bulb having a longitudinal axis. By way of example, in this embodiment radiation sources 7a and 7b might each be a six-inch long, 2400-watt ultraviolet lamp. Radiation sources 7a and 7b are positioned within troughs 1a and 1b, respectively. Each of troughs 1a and 1b preferably is substantially one half of an ellipse, although each trough could be less or more than one half of an ellipse if desired. Each ellipse has a respective major axis 27a and 27b. As depicted in FIG. 11, the major axes 27a and 27b of the ellipses of troughs 1a and 1b of apparatus 13a intersect at an angle θ in front of the troughs. The angle θ might be in the range of from 0° to 90°, preferably from about 5° to about 35°. FIG. 11 depicts a preferred angle θ of 20°.

Radiation source 7a irradiates elongated curved objects 17. The ellipse of trough 1a has a first focal point within the trough. The locus of the first focal point along the length of trough 1a defines a first focal axis of trough 1a. Radiation source 7a is spaced from the first focal axis of trough 1a at a position on the major axis 27a of the ellipse of trough 1a that results in optimum two-dimensional uniformity of the radiation distribution on elongated curved objects 17. This might be a position toward elongated curved objects 17 by, for example, about ten percent of the focal length of the ellipse. In like manner, radiation source 7b irradiates elongated curved objects 17. The ellipse of trough 1b has a first focal point within the trough. The locus of the first focal point along the length of trough 1b defines a first focal axis of trough 1b. Radiation source 7b is spaced from the first focal axis of trough 1b at a position on the major axis 27b of the ellipse of trough 1b that results in optimum two-dimensional uniformity of the radiation distribution on elongated curved objects 17. This might be a position toward elongated curved objects 17 by, for example, about ten percent of the focal length of the ellipse.

Each trough 1a and 1b is similar to trough 1 of the embodiment of FIGS. 1–9. Thus, elliptical reflecting trough 1a terminates in a right side edge and a left side edge. These edges of trough 1a define a plane which is substantially perpendicular to the major axis 27a of the ellipse of trough 1a and substantially parallel to the longitudinal axis of radiation source 7a. Substantially, flat upper elliptical reflector 20a of trough 1a terminates in an upper angled edge. Similarly, substantially flat lower elliptical reflector 21a of trough 1a terminates in a lower angled edge. In like manner, elliptical reflecting trough 1b terminates in a right side edge and a left side edge. These edges of trough 1b define a plane which is substantially perpendicular to the major axis 27b of the ellipse of trough 1b and substantially parallel to the longitudinal axis of radiation source 7b. Upper elliptical reflector 20b of trough 1b terminates in an upper angled edge. Similarly, lower elliptical reflector 21b of trough 1b terminates in a lower angled edge.

A substantially flat upper middle reflector 18a extends from the upper angled edges of troughs 1a and 1b to the inner edge of a substantially flat upper outer reflector 19a. Upper outer reflector 19a extends from upper middle reflector 18a toward objects 17. In like manner, a substantially flat lower middle reflector 18b extends from lower angled edges of troughs 1a and 1b to the inner edge of a substantially flat lower outer reflector 19b. Lower outer reflector 19b extends from lower middle reflector 18b toward objects 17. A substantially flat right outer reflector 22a extends from the right side edge of trough 1a toward objects 17, and a substantially flat left outer reflector 22b extends from the left or second side edge of trough 1b toward objects 17. Preferably, the left side edge of trough 1a contacts the right side edge of trough 1b over the length of these vertical edges. Alternatively, these edges are joined by a reflective vertical panel so as to prevent escape of radiation.

Although in FIGS. 11–14 and the related description troughs 1a and 1b and elongated discharge bulbs 7a and 7b are depicted and described as having their longitudinal axes extending vertically, the axes could extend horizontally or at an angle, if desired.

Figure 15:
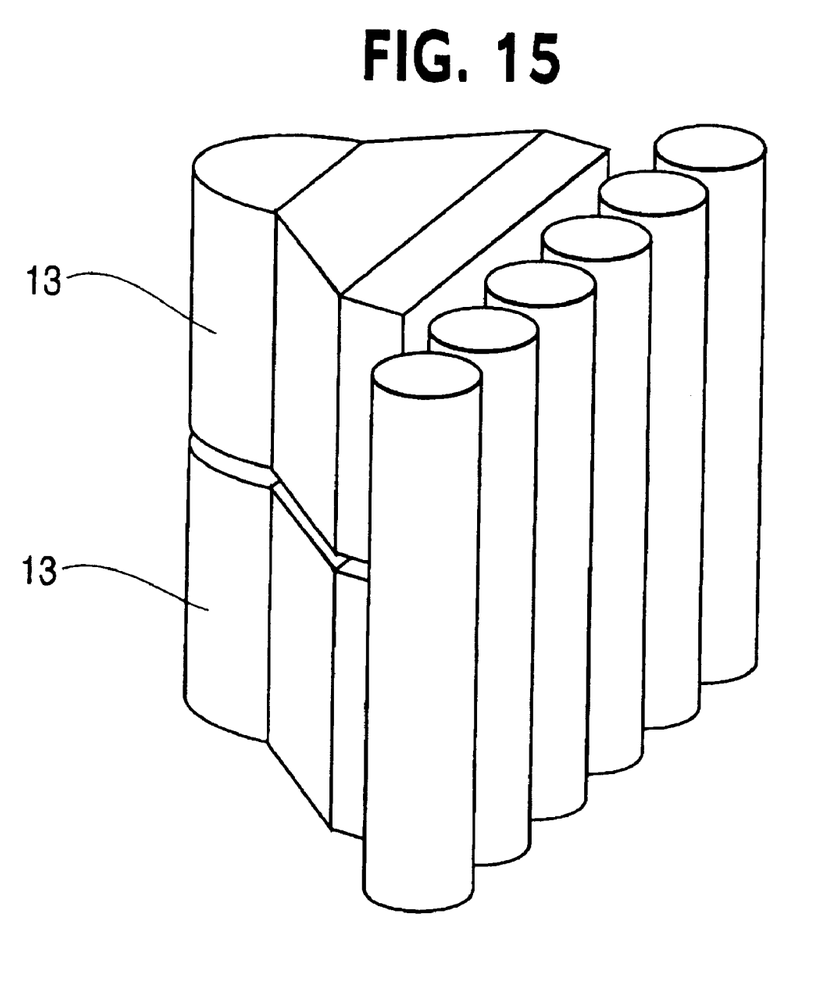
FIG. 15 is an isometric view of a third embodiment of an apparatus for providing substantially two-dimensionally uniform irradiation of an elongated curved object surface in accordance with the present invention.

FIG. 15 depicts a third embodiment of an irradiation apparatus in accordance with the present invention. This embodiment includes at least two of the devices 13 described in the first embodiment of FIGS. 1–9, stacked one on the top of another to irradiate longer objects.

To show the advantages of the present invention, the following examples were obtained using computer simulations.

EXAMPLE 1

Figure 16:
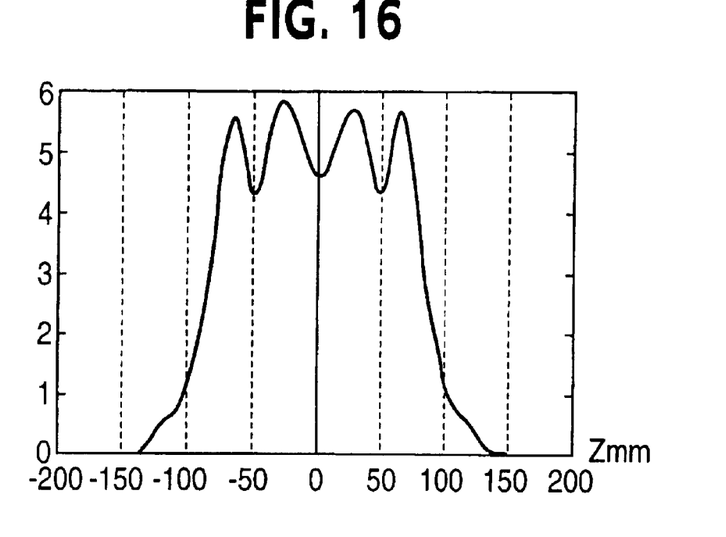
FIGS. 16 and 17 are graphs illustrating the operation of the embodiment of FIG. 1.
Figure 17:
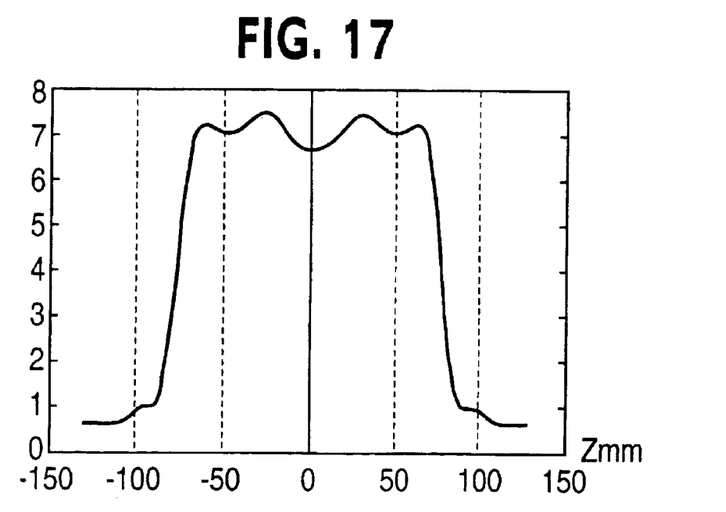

An apparatus in accordance with FIGS. 1–9 includes an elongated irradiation source 7 in the form of a six-inch long, 2400-watt tubular microwave powered ultraviolet discharge bulb. The source 7 is in an associated trough 1. The trough 1 is one half of an ellipse having a major axis of approximately six inches and a minor axis of approximately four inches. Radiation source 7 is positioned approximately 0.15 inch from the first focal axis 10 of the trough 1 toward a set of elongated objects 17, for example, cans or the cylindrical parts of bottles, each of which has a radius R=1.13 inches and a height of 6 inches. Reflectors 4a, 4b, 5a, and 5b are pivoted on pivotable mounts 28 to further optimize the uniformity of the radiation distribution. Objects 17 are moved at approximately 36 centimeters per second and are rotated at approximately 2 revolutions per second. FIG. 16 depicts the distribution of the radiation reaching the surfaces of objects 17 along the horizontal direction or direction across the irradiator, while FIG. 17 depicts the distribution of the radiation reaching the surfaces of objects 17 along the vertical direction or direction along the irradiator. The directions are shown in FIG. 1. As can be seen from FIGS. 16 and 17, the distribution of the radiation is substantially uniform.

EXAMPLE 2

Figure 18:
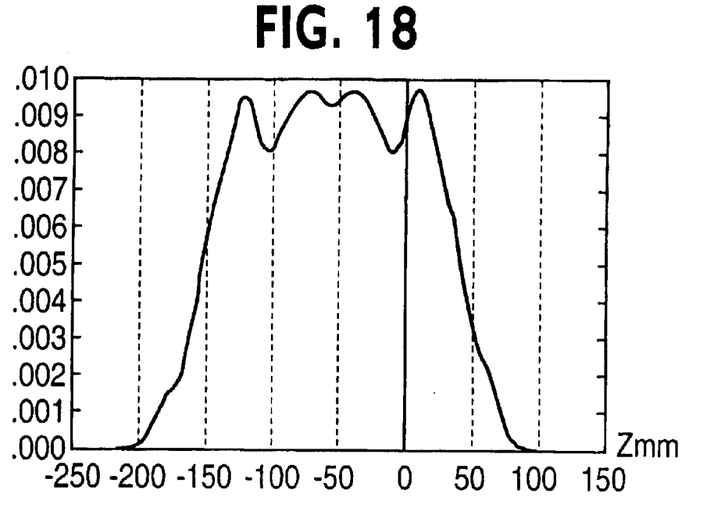
FIGS. 18 and 19 are graphs illustrating the operation of the embodiment of FIG. 11.
Figure 19:
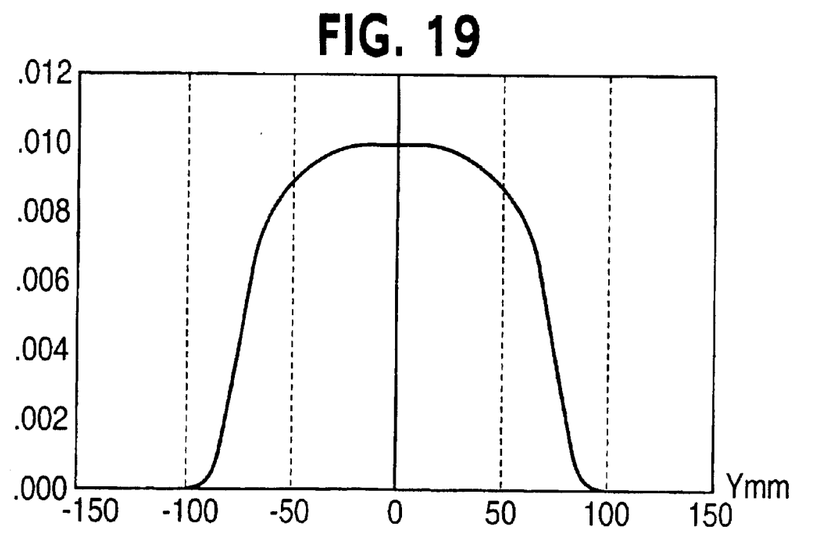

In an apparatus having two radiation sources in two associated troughs, as depicted in FIGS. 11–14, each of radiation sources 7a and 7b is a six-inch long, 2400-watt tubular microwave powered ultraviolet discharge bulb. The sources 7a and 7b are in associated troughs 1a and 1b. Each trough is one half of an ellipse having a major axis of approximately six inches and a minor axis of approximately four inches. Radiation sources 7a and 7b are positioned approximately 0.15 inch from the respective first focal axes of the troughs toward a set of elongated objects 17, for example, cans or the cylindrical parts of bottles each of which has a radius R=1.13 inches and a height of 6 inches. Objects 17 are moved at approximately 36 centimeters per second and rotated at approximately 2 revolutions per second. FIG. 18 depicts the distribution of the radiation reaching the surfaces of objects 17 along the horizontal direction or direction across the irradiator, while FIG. 19 depicts the distribution of the radiation reaching the surfaces of the objects 17 along the vertical direction or direction along the irradiator. As can be seen from FIGS. 18 and 19, the distribution of the radiation is substantially uniform.

It can thus be seen that the present invention is an apparatus for and a method of providing substantially two-dimensionally uniform irradiation of elongated three-dimensional objects with a high level of irradiance. Although the present invention has been described with reference to preferred embodiments, various rearrangements, alterations, and substitutions might be made, and still the result would be within the scope of the invention.

What is claimed is:

1. An apparatus for providing substantially two-dimensionally uniform irradiation of elongated three-dimensional objects with a high level of irradiance, said apparatus comprising:
    a source of radiation for producing radiation to irradiate the surface of an elongated three-dimensional object;
    an elongated elliptical reflecting trough for reflecting light from said source of radiation and concentrating the reflected light on the surface of the object, the transverse cross-section of said trough being a portion of an ellipse having a major axis and a minor axis, said trough having a focal axis within the trough, said source of radiation being within said trough, on the major axis and spaced from the focal axis of said trough, said trough terminating in an opening defining a rectangular plane substantially perpendicular to the major axis of the ellipse of said trough and substantially parallel to the longitudinal axis of said source of radiation, said trough opening having upper and lower edges and right and left side edges;
    a substantially flat upper elliptical reflector connected to the upper edge of said trough and having a forward edge;
    a substantially flat lower elliptical reflector connected to the lower edge of said trough and having a forward edge;
    a substantially flat upper middle reflector extending from the forward edge of said upper elliptical reflector;
    a substantially flat lower middle reflector extending from the forward edge of said lower elliptical reflector;
    a substantially flat right side middle reflector extending from the right side edge of said trough;
    a substantially flat left side middle reflector extending from the left side edge of said trough;
    a substantially flat upper outer reflector extending from said upper middle reflector;
    a substantially flat lower outer reflector extending from said lower middle reflector;
    a substantially flat right side outer reflector extending from said right side middle reflector; and
    a substantially flat left side outer reflector extending from said left side middle reflector.

2. Apparatus as claimed in claim 1, further comprising mounts pivotally mounting at least some of said reflectors, permitting adjustment of the angular positions of the pivotally mounted reflectors relative to said trough.

3. A method of providing substantially two-dimensionally uniform irradiation of elongated three-dimensional objects with high level of irradiance, said method comprising:
    providing the apparatus of claim 2;
    adjusting the angular positions of the pivotally mounted reflectors relative to the trough;
    activating the source of radiation; and
    moving the objects linearly across said apparatus while rotating the objects about their respective longitudinal axes.

4. Apparatus as claimed in claim 1, wherein said source of radiation is an elongated discharge bulb.

5. Apparatus as claimed in claim 1, wherein said source of radiation is a light source.

6. Apparatus as claimed in claim 5, wherein said light source is a source of ultraviolet light.

7. Apparatus as claimed in claim 6, wherein said source of ultraviolet light is a microwave electrodeless discharge bulb.

8. Apparatus as claimed in claim 7, wherein said bulb is tubular bulb.

9. Apparatus as claimed in claim 6, wherein said source of ultraviolet light is an arc discharge bulb.

10. Apparatus as claimed in claim 6, wherein said source of ultraviolet light is a fluorescent discharge bulb.

11. Apparatus as claimed in claim 1, wherein said source of radiation is located on the major axis of the respective trough.

12. Apparatus as claimed in claim 1, wherein said trough includes a mount adjustably mounting said source of radiation for movement along the major axis of the ellipse of said trough.

13. A method of providing substantially two-dimensionally uniform irradiation of elongated three-dimensional objects with high level of irradiance, said method comprising:
    providing the apparatus of claim 12;
    adjusting the position of the source of radiation along the major axis of the trough;
    activating the source of radiation; and
    moving the objects linearly across said apparatus while rotating the objects about their respective longitudinal axes.

14. An apparatus for substantially two-dimensionally uniform irradiation of elongated three-dimensional objects with high level of irradiance, said apparatus comprising:
    first and second substantially identical elongated reflecting troughs, each trough extending longitudinally from a first end to a second end, the transverse cross-section of each trough being a portion of ellipse having a major axis and a minor axis, each trough having a focal axis within the trough and having first and second side edges, said first and second troughs being positioned with the major axes of their ellipses intersecting at an angle $\theta$, where $0° \leq \theta \leq 90°$, substantially flat first and second upper elliptical reflectors connected to the first ends of said first and second troughs respectively;

substantially flat first and second lower elliptical reflectors connected to the second ends of said first and second troughs respectively;

a first radiation source having a longitudinal axis extending substantially parallel to the first focal axis of said first trough, said first radiation source being within said first trough and spaced from the first focal axis of said first trough;

a second, substantially identical radiation source having a longitudinal axis extending substantially parallel to the first focal axis of said second trough, said second radiation source being within said second reflecting trough and spaced from the first focal axis of the second trough;

a substantially flat upper middle reflector extending from the first and second upper elliptical reflectors;

a substantially flat lower middle reflector extending from the first and second lower elliptical reflectors;

a substantially flat upper outer reflector extending from said upper middle reflector;

a substantially flat lower outer reflector extending from said lower middle reflector;

a substantially flat right side outer reflector extending from the right side edge of said first trough; and a substantially flat left side outer reflector extending from the left side edge of said second trough.

15. An apparatus as claimed in claim 14, wherein $5° \leq \theta \leq 35°$.

16. An apparatus as claimed in claim 15, wherein $\theta = 20°$.

* * * * *